(12) United States Patent
Sinofsky

(10) Patent No.: US 12,053,642 B2
(45) Date of Patent: Aug. 6, 2024

(54) METHOD AND DEVICES FOR INFRARED THERAPY

(71) Applicant: Edward Sinofsky, Dennis, MA (US)

(72) Inventor: Edward Sinofsky, Dennis, MA (US)

(73) Assignee: Edward Sinofsky, Dennis, MA (US)

( * ) Notice: Subject to any disclaimer, the term of this patent is extended or adjusted under 35 U.S.C. 154(b) by 918 days.

(21) Appl. No.: 17/049,465

(22) PCT Filed: Apr. 26, 2019

(86) PCT No.: PCT/US2019/029344
§ 371 (c)(1),
(2) Date: Oct. 21, 2020

(87) PCT Pub. No.: WO2019/210164
PCT Pub. Date: Oct. 31, 2019

(65) Prior Publication Data
US 2021/0252306 A1 Aug. 19, 2021

Related U.S. Application Data

(60) Provisional application No. 62/662,994, filed on Apr. 26, 2018.

(51) Int. Cl.
*A61N 1/00* (2006.01)
*A61N 5/06* (2006.01)

(52) U.S. Cl.
CPC .... *A61N 5/0625* (2013.01); *A61N 2005/0645* (2013.01); *A61N 2005/0659* (2013.01); *A61N 2005/0665* (2013.01)

(58) Field of Classification Search
CPC .......... A61N 5/0625; A61N 2005/0645; A61N 2005/0659; A61N 2005/0665; A61F 2007/0009; A61F 2007/0029
See application file for complete search history.

(56) References Cited

U.S. PATENT DOCUMENTS 4,930,504 A * 6/1990 Diamantopoulos .. A61N 5/0616
250/494.1
5,591,447 A 1/1997 Jensen
(Continued)

FOREIGN PATENT DOCUMENTS

WO 2010028740 A1 3/2010
WO 2019210164 A1 10/2019

OTHER PUBLICATIONS

International Preliminary Report on Patentability, PCT/US2019/029344, dated Oct. 27, 2020, 12 Pages.
(Continued)

*Primary Examiner* — Scott M. Getzow
(74) *Attorney, Agent, or Firm* — Potomac Law Group, PLLC; Reza Mollaaghababa

(57) ABSTRACT

Methods and devices are disclosed for infrared phototherapy. The device can include a flexible substrate, a plurality of infrared light sources associated with the substrate and a drive circuitry configured to couple to a power supply and connected to the light sources to activate the light sources to emit infrared radiation. The device can be positioned on a subject's body to transmit infrared radiation to a target region of skin or muscle tissue of a subject to raise the temperature of the target region above normal body temperature. The plurality of light sources can be disposed in a spaced-apart relationship on the substrate such that collectively they emit infrared radiation in an overlapping pattern that provides for substantially uniform exposure of a target region. The substrate can be actively cooled to control the surface temperature of the target region. The device can further include a light-transmissive sealing element to isolate the LEDs from contact with the subject's body.

35 Claims, 6 Drawing Sheets

(56) References Cited

U.S. PATENT DOCUMENTS

| | | | |
|---|---|---|---|
| 5,905,269 | A | 5/1999 | Venkataramani et al. |
| 6,743,249 | B1 * | 6/2004 | Alden ................. A61N 5/0601 606/1 |
| 2003/0038292 | A1 | 2/2003 | Wang et al. |
| 2007/0208395 | A1 * | 9/2007 | Leclerc ................ A61N 5/0616 607/86 |
| 2007/0239232 | A1 * | 10/2007 | Kurtz ..................... G02B 6/001 607/87 |
| 2008/0300529 | A1 | 12/2008 | Reinstein |
| 2010/0049180 | A1 * | 2/2010 | Wells .................. A61N 5/0616 606/11 |
| 2013/0165837 | A1 | 6/2013 | Addison et al. |
| 2015/0112411 | A1 | 4/2015 | Beckman et al. |
| 2015/0165228 | A1 | 6/2015 | Lemmens et al. |
| 2017/0100585 | A1 | 4/2017 | Hall et al. |
| 2018/0030626 | A1 | 2/2018 | Chen et al. |

OTHER PUBLICATIONS

International Search Report and Written Opinion, PCT/US2019/029344, dated Aug. 7, 2019, 14 pages.

* cited by examiner

METHOD AND DEVICES FOR INFRARED THERAPY

REFERENCE TO RELATED APPLICATIONS

This Application is a section 371 U.S. national stage filing of International Application No. PCT/US2019/029344, filed Apr. 26, 2019 that claims priority to, and the benefit of, U.S. Provisional Application No. 62/662,994, filed on Apr. 26, 2018, the disclosures of which are herein incorporated by reference in their entirety.

FIELD

The technical field of the invention is phototherapy and, in particular, light-based therapy for muscle pain, soreness, or osteoarthritis, as well as inflammation reduction, neurological, muscular and/or other body conditions.

BACKGROUND

Infrared LED therapies are well known in the art. LED arrays are typically rigid with the LEDs tightly packed together. These devices are usually fixed sources requiring the patient to remain still. They are typically not used in contact with the tissue. Rapid spreading of the light due to the LED's large divergence angle can result in treatment inefficiency as much of the emitted light misses the target. A large percentage of this light, perhaps as much as 40 percent, is also reflected by back scattering off the surface or from subsurface tissue layers, making the treatment even more inefficient.

A long felt need in the art would be "wearable" light therapy devices that allow the patient to move during the therapy and/or devices that can increase the efficiency of light delivery to target tissue.

SUMMARY

Methods and devices are disclosed for infrared phototherapy for muscle pain, soreness, or osteoarthritis, as well as inflammation reduction, neurological, muscular and/or other body conditions. Lower power embodiments of the invention can be useful in LLT (low level light therapy). Higher power embodiments of the invention can be used to shrink or eliminate fat cells, induce cell necrosis or to de activate nerve cells in the treatment of chronic pain.

The devices can include a substrate, a plurality of infrared light sources associated with the substrate and electrical drive circuitry connected to the light sources to couple to a power supply and activate the light sources to emit infrared radiation. The substrate and circuitry can be flexible and/or adaptable for positioning on a subject's body to transmit infrared radiation to a target region of skin, muscle tissue, or a joint of a subject to raise the temperature of the target region above normal body temperature or to administer LLT. In some embodiments, the plurality of light sources are preferably disposed in a spaced-apart relationship on the substrate such that, collectively, they emit infrared radiation in an overlapping pattern that provides for substantially uniform exposure of a target region.

The devices of the present invention can be flexible or conformable in at least one dimension, preferably in at least two dimensions, to follow a contour of the subject's body and assure efficient treatment (e.g., heating) of the tissue. The source spacing can be chosen, as it relates to the cumulative illumination from multiple emitters, to produce substantially uniform irradiation of the target. Reflective surfaces between the emitters can recycle light reflected by the target region back into the tissue making the treatment even more energy efficient. This increase in efficiency can facilitate operation of the device with little or no active cooling in low and mid power applications, and less active cooling at the higher power settings.

The devices of the present invention can also include one or more sealing elements to make the devices water resistant or otherwise protect the LEDs and drive circuitry from liquid spills, water immersion or contact will other undesirable materials. The substrate and circuitry can be encapsulated by a sealing element, or sandwiched between two or more sealing elements. For example, the substrate and drive circuitry can be disposed between a posterior (e.g., outer) shaping element and an anterior (e.g., inner) light-transmitting element. In certain embodiments, the posterior shaping element can be a shape-memory element. In certain embodiments, the anterior element can be formed as one or more transparent or translucent windows on the device surface proximal to the target tissue region. The sealing element(s) can also permit the device to be effectively cleaned and sterilized. The sealing element can comprise, for example, silicone, polyethylene terephthalate (PET), polyethylene terephthalate gylcol (PETG), ultra-high molecular weight (UHMW) polyethylene, or a fluoropolymer.

The devices can further include one or more compressible layers to provide padding or a cushion to protect the LEDs and circuitry from damage from undesirable pressure. In certain embodiments, the substrate itself is compressible and provides this protective feature. The devices can be held to the skin by a variety of mechanisms including tacky or adhesive surface layers, adhesive tape, sleeves (including gloves or other garments), Velcro® straps or the like.

In one aspect of the invention, the devices can include two or more infrared LEDs in a spaced relationship designed to evenly heat or otherwise treat tissue uniformly while being conveniently attached (or disposed proximal) to the subject's body. The LEDs can be spread apart at distances that approximate the radius of an LED's wide illuminated glow-ball in order to substantially uniformly illuminate the tissue at depth. (The term "glow ball" is used herein to describe a spherical or partially spherical projection surrounding a light source within which the power is at least 1/e of the maximum radiant power of the source.)

When light is delivered to tissue, it can be simultaneously absorbed and scattered. The higher the absorption the lower the amount of scattering. Using moderate to low absorption wavelengths allows deep penetration of the light, on the order of a centimeter, below the surface of the target region. The scattering at these distances can be significant. The resultant distribution of light in the tissue is a luminous glow ball with a diameter significantly wider than the light at the source. These light distributions follow an almost Gaussian drop in intensity as one moves away from the source.

A boundary for each light source can be defined by its 1/e power level. For the wavelengths of interest (e.g., wavelengths around 800 nm), the 1/e power level is about 8-9 mm from the center of the source. The power contributed by each LED at the 1/e boundary is ~37% of its maximum. If the sources are spread apart by about two times this distance then the two 1/e boundaries overlap. Thus, the combined power where the 1/e boundaries meet between the sources is ~37%+~37%, or about 75% of maximum power deliverable to tissue closest to each emitter. The cumulative effect of this preferred spacing is the delivery of a substantially uniform intensity distribution to the target region of tissue.

A white reflective or diffusive sheet, e.g., a white background) can be deployed above or surrounding the light source to further homogenize the distribution.

In two-dimensional arrays of light sources, the separation between rows of light sources (in both the x and y dimensions) can be set at the same distance apart, creating a substantially uniform distribution of light in a two-dimensional plane. For example, if each LED emits a glow-ball of 8-9 mm in radius, the LEDs can be spaced about 17 mm from each other in either a stacked or checker-board type pattern to provide uniform treatment of a two-dimensional target region.

In certain embodiments, the LEDs emit infrared radiation of at least one wavelength in a range from 700 to 900 nanometers. For example, the LEDs can emit radiation at about 805 nm. The light sources can generate about 25-1000 milliwatts of power. (Typically, the term "about" as used herein means greater or lesser than the value or range of values stated by $^1/_{10}$ of the stated values, e.g., .+−.10%.)

The devices can further include a controller for setting a plurality of power levels to change the intensity of the emitted infrared radiation. For example, at low power the illumination can be used as a source in low level light therapy. At moderate power, the array can be used for therapeutic heating of the tissue for pain relief and use in combined heat/cool therapy. At higher power the unit can induce fat cell killing and melting in cosmetic procedures or nerve deactivation in the treatment of chronic pain.

The device can further include a garment-like element (referred to herein as a "sleeve") adapted to wrap around a body part and hold the substrate and light sources in a desired position relative to the target region. In certain embodiments the sleeve can also include a thermally conductive element such as copper fibers to dissipate heat during device operation.

The devices can further include a coupling element that has a contour to assist in coupling to a subject's body. For example, the contour can be curved or arch-shaped to make it easy to apply the device to target areas such as the neck, knee, ankle, wrist, arm or leg. In some embodiments, the coupling element can also include a shape-memory component such that the coupling element retains a desired shape. Alternatively, the coupling element can also be formed into a desired shape without a shape-memory element, and held in proximity to the target region by conventional means, e.g., Velcro® straps or the like.

Other variations of the device include one or more transparent or translucent windows between the LEDs and the subject's body, e.g., windows that can cover and/or seal holes in the reflective thermal pad that are aligned with the array of LEDs. The window(s) can also protect the LEDs from direct pressure being applied to their delicate circuitry. In further embodiments, the window can be implemented as a single, irradiation-transmissive, sheet that covers all or a substantial portion of the substrate's anterior surface.

In certain embodiments, the substrate can include a plurality of recesses into which the light sources (LEDs) are disposed. The substrate can also include a reflective component to return reflected or backscattered radiation back into the target region. For example, the substrate can be a flexible polymeric material, such as silicone, and the reflective component can be reflective filler particles, e.g., titanium oxide or barium particles in the polymer. In certain preferred embodiments, the substrate is both radiation-reflective and thermally conductive to further contribute to uniform heating of a target tissue region. Such substrates can also include adhesives on one or both surfaces, e.g., for posterior mounting to a circuit board and/or anterior mounting to a window or cover sheet.

In another aspect of the invention, methods of providing phototherapy are disclosed by applying a flexible substrate carrying a plurality of infrared light sources to the body of a patient. The light sources being disposed in a spaced-apart relationship from each other on the substrate such that upon activation they collectively emit infrared radiation in an overlapping pattern that provides for substantially uniform exposure of a target region; and activating the light sources to transmit infrared radiation to the target region of skin or muscle tissue of a subject to uniformly raise the temperature of the target region above normal body temperature.

The method can be practiced by delivering infrared radiation of at least one wavelength in a range from 700 nm to 900 nm, e.g., 805 nm to the target region. The radiation can be delivered at a power ranging from about 50-1000 milliwatts, or preferably between 100-300 milliwatts per light source when activated. The method can further include adjusting a power level of the light sources to change the intensity of the emitted infrared radiation.

The method can also be practiced by including a transparent or translucent cover that both seals the LED from liquids and also protects the LED from pressure being applied to it.

The method can further be practiced by deploying a sleeve adapted to wrap around a body part to hold the substrate and light sources in a desired position relative to the target region. The sleeve can include a thermally connective component to dissipate heat. In certain embodiments, the substrate can have a reflective component and the method can further include utilizing the reflective component to return reflected or backscattered radiation back into the target region.

The method can also be practiced by the application of the flexible device to the target region by mounting it to contoured coupling element that preferably has shape memory, like a metal or plastic hairband. Alternatively, the devices can be formed without a contoured coupling agent (e.g., without plastic or metal shape-memory element) and can be held to the target with adhesives, adhesive bandages, or Velcro® type hook and loop fastener bands.

The method can also be practiced by adding active cooling capability. By the addition of a heatsink with a fan, or thermoelectric (e.g., a Peltier thermoelectric device) cooling of the substrate one can either cool the surface of the tissue simultaneously with the application of the infrared or alternately in a heating-cooling therapy regime.

DETAILED DESCRIPTION

Figure 1A:
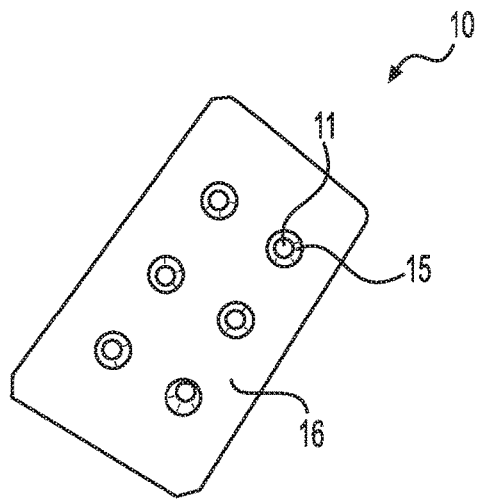
FIG. 1A is a plan view of an infrared therapy device according to the invention.
Figure 1B:
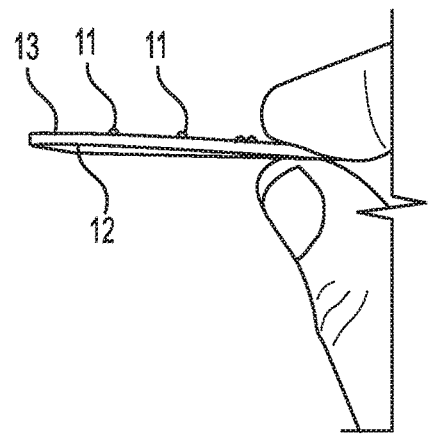
FIG. 1B is a side view of the infrared therapy device of FIG. 1A.
Figure 1C:
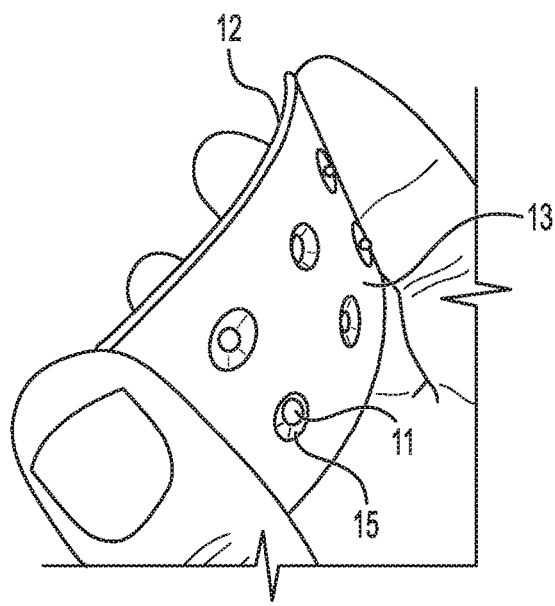
FIG. 1C is a perspective view of the infrared therapy device of FIG. 1A showing flexure.
Figure 1D:
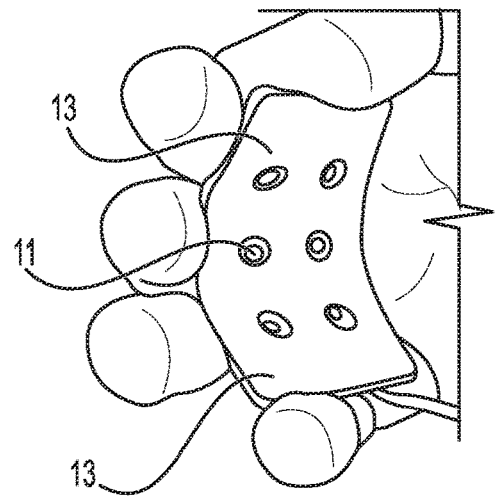
FIG. 1D is a perspective view of the infrared therapy device of FIG. 1A showing flexure in an orthogonal direction.

FIGS. 1A-1D show a device 10 according to the invention including LEDs 11 mounted on flexible substrate 13. One suitable LED is the SMD 3535IR810 produced by ShenZen Hanhua Opto Co. The substrate 13 can be, for example, a silicone sheet that is approximately 1-3 mm thick and has holes cut into it to allow the emission of light therethrough. These diameter of these holes can be slightly larger than the size of an LED, in this case, about 4 mm. The sheet can also include reflective particles like $TiO_2$ (titanium dioxide) or reflective, thermally conductive particles like $BaSO_4$ (barium sulfate) or $AlO_3$ (alumina). In the illustrated embodiment, a flexible circuit board 12 with drive circuitry and surface mounted LEDs in the desired size is then affixed to one side of a substrate sheet 13. The opposition side of the substrate (i.e., the anterior side that will face a target region of the subject's body) can then be covered with a light-transmissive sheet (now shown). Alternatively the entire device can be encapsulated by adding a sealing element, such as a light transmissive film around the entire device.

In certain embodiments, the LEDs can be infrared LEDs capable of receiving 0.1 to 3 Watts of electrical power. In certain embodiments, the LEDs can be run at lower or higher powers. When operating at 3 W of electrical input, about 1 W of IR power is typically produced. For low level light applications the IR power output per LED can be about 25 mw. For mid power applications 100-300 mw/LED can be produced. For high power applications, the full 1 W of power output per LED (or higher) can be utilized.

The anterior device surface (proximal to the target region of subject's body) has an emission area (15) and an interstitial area (16). The interstitial area is a high fraction of the device's total anterior surface area. As an example, for a 6 LED patch of size 30×60 mm, the emission area/total area is 4%. The placement of the LEDs and the extent of the interstitial areas are designed such that the spacing of the LEDs is about twice the 1/e radius of the illuminated glow ball of each LED.

As explained in more detail below, the LEDs can be energized by DC electricity via a cable that couples the device to a power source. The power source can be, for example, a USB power source, an AC/DC power supply or a battery. Alternatively, the energy source can be built into the device itself (e.g., using low-profile LiIon batteries or the like).

In low level light applications (LLT) the LEDs can operate at such low power that no additional heat sinking is needed. The circuit board and the tissue both remain near body temperature. In a medium power applications for treatment of inflammation and pain, heat from the circuit board can be dissipated into the tissue through the silicone sheet. At these power levels the waste heat from the LEDs can warm the circuit board to at near body temperature or slightly above body temperature. Since the goal of this treatment is to heat the tissue, it can be advantageous to permit heat conduction from the LEDs and circuit board through the silicone sheet into the tissue.

Since in low and medium power applications the flow of heat into the target region is desirable, heating can be further facilitated by reflective materials embedded in the substrate such as the $TiO_2$ (titanium oxide). The reflective scattering agent can have enhanced thermal properties as well as reflective properties, such as $BaSO_4$ (barium sulfate) or alumina.

In higher power applications, the objective is often to raise the temperature of the tissue below the surface to cause deep heating while not burning the skin. In these embodiments, heat can be removed from the tissue surface in various ways beyond conductive or convective dissipation into the ambient environment. This can be done by enhancing the heat sinking at the circuit board by adding further heat extraction capabilities. Heat extraction can be either passive, such as normal metallic or ceramic heatsinks, or active by cooling with a fan thermoelectric, or water cooled device that has its own heat sinking capability. The net flow of heat in this higher power application is away from the tissue surface and into the ambient.

In LLT and Medium power applications the device can be extremely light and thin and can be held in contact with the tissue in several ways that take advantage of the thin dimension and the flexibility of the device. The easiest way is for the patient to simply hold the device to the region of the body to be treated. If this is inconvenient, the device can further include an adherent anterior surface, e.g., a coating of suitable adhesive or a skin-contacting surface with a "soft tack" material. For example the anterior surface can be at least partially coated with a silicone gel, to impart the desire degree of tackiness. Soft-tack silicone coating compositions can be formed using silicone elastomers available from Dow Corning under product reference Q7-9177. Additional details on applying silicone coatings can be found in U.S. Patent Application Pub. No. 2013/0165837 by Systagenix Wound Management IP Co. BV entitled "Silicone Gel-Coated Wound Dressings," published Jun. 27, 2013, herein incorporated in its entirety by reference. (The tacky surface can be preserved by a cover sheet until the device is ready to be used.)

Alternatively, the devices can be held in place by medical tape or surrounded by a retaining or compression sleeve placed around the body part to be treated. In another embodiment various combinations of adhesive tape and other mechanisms (e.g., shape-memory elements or magnetic attraction) can be used to hold the patch in place.

Figure 2A:
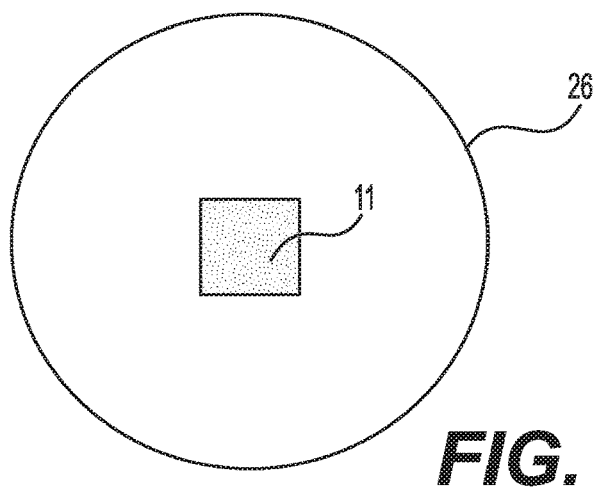
FIG. 2A shows an illustration of a glow ball from a single LED.

FIG. 2A illustrates the "glow ball" 26 associated with a single LED element 11 in the present invention. (As noted above, the spherical or partially spherical projection surrounding a light source within which the power is at least 1/e of the maximum radiant power at the source itself is referred to herein as the "glow ball" of the source.)

Figure 2B:
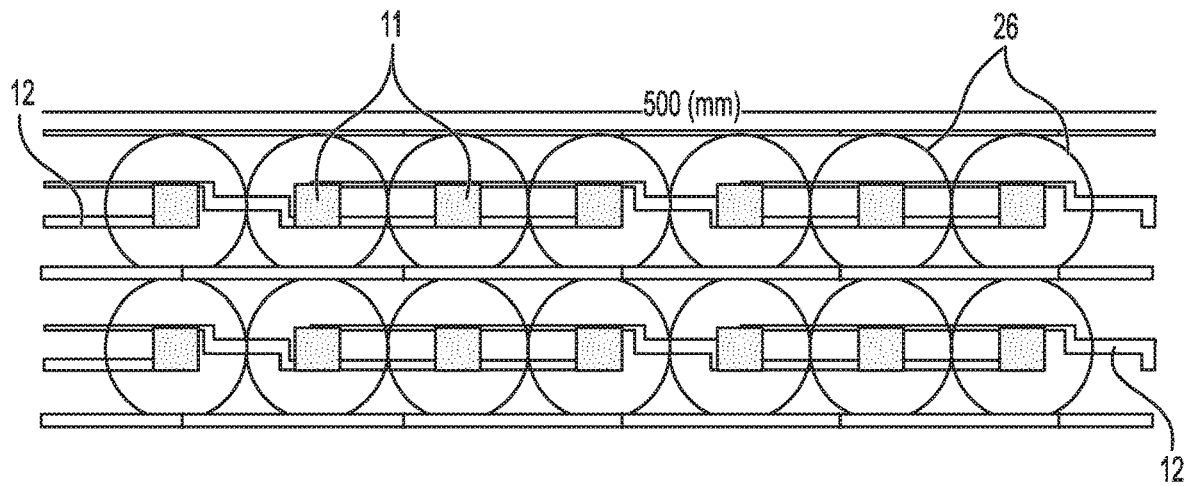
FIG. 2B shows how 1/e points overlap on an array of LEDs.

FIG. 2B illustrates an array of LEDs according to the invention connect to their driver circuitry 12 (e.g., on a flexible circuit board) Again, the glow ball for each light source 11 can be defined by its 1/e power level boundary 26. For the wavelengths of interest (e.g., wavelengths around 800 nm), the 1/e power level is about 8-9 mm from the center of the source. The power contributed by each LED at the 1/e boundary is ~37% of its maximum. If the sources are spread apart by about two times this distance then the two 1/e boundaries overlap. Thus, the combined power where the 1/e boundaries meet between the sources is ~37%+ ~37%, or about 75% of maximum power deliverable to tissue closest to each emitter. The cumulative effect of this preferred spacing is the delivery of a substantially uniform intensity distribution to the target region of tissue.

Figure 3:
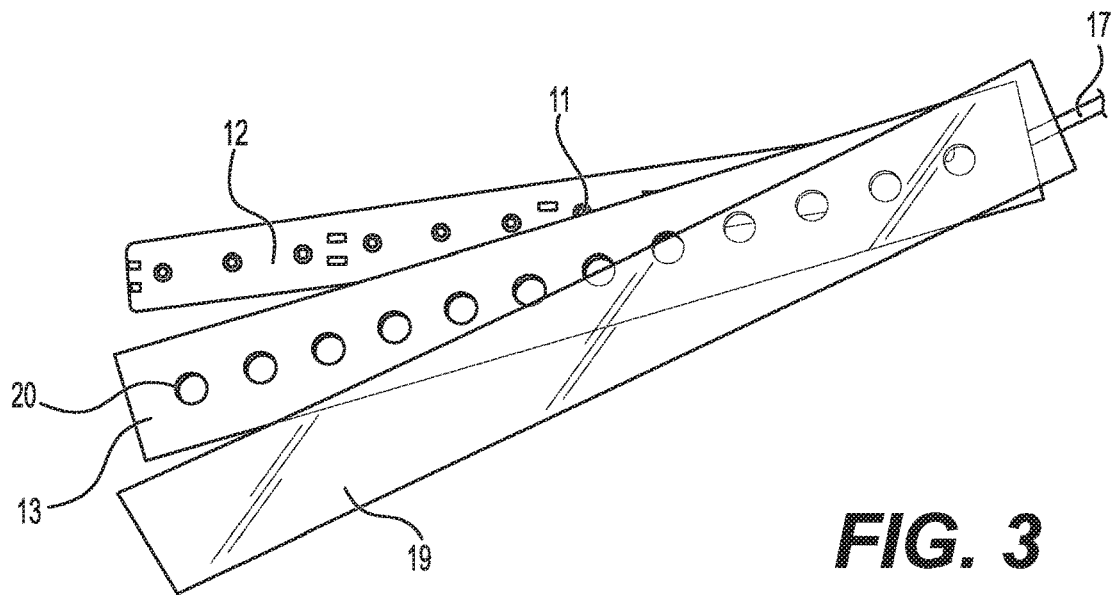
FIG. 3 illustrates the various layers of one embodiment of a device according to the invention.

FIG. 3 shows an embodiment of the invention in which the device is constructed in three layers as a sealed patch. The driver circuitry 12 is incorporated into flexible circuit board that forms the posterior device layer. The LEDs 11 are mounted on the circuit board in electrical contact with the drive circuitry. A thermal pad (13) with recesses or holes 20 cut for the LEDs forms the middle (or substrate) layer. The opposite side of the pad is then covered by a translucent or transparent layer 19 that seals the LED against dirt and moisture. It also provides a flat surface to contact human tissue for a well-defined dosimetry as it holds the LEDs from the surface at a well-defined distance determined by the thickness of the thermal pad. The anterior surface of the window layer 19 can be covered with a skin adhesive material or the device can be fitted with a skin coupling mechanism, such as straps with Velcro®-type fasteners.

Alternatively, the window layer 19 can be made of a tacky light-transmissive material (e.g., transparent or translucent silicone) with a removable cover sheet (not shown) to permit direct skin adhesion when the cover sheet is removed. The three layers can thus form a laminate that can be produced flat. Alternatively, the stacked layers can be molded into a convex shape (LEDs on the inside of a curve) or a concave shape (LEDs on the outside of the curve) device. The layers are preferably sealed together to form a water-impervious construction.

Alternatively, two layer constructions can be formed by the circuit layer 12 and substrate 13 with the holes in substrate layer 13 fitted with individual window plugs. In this embodiment, the substrate itself provides the anterior (skin-contacting) surface of the device.

Figure 4A:
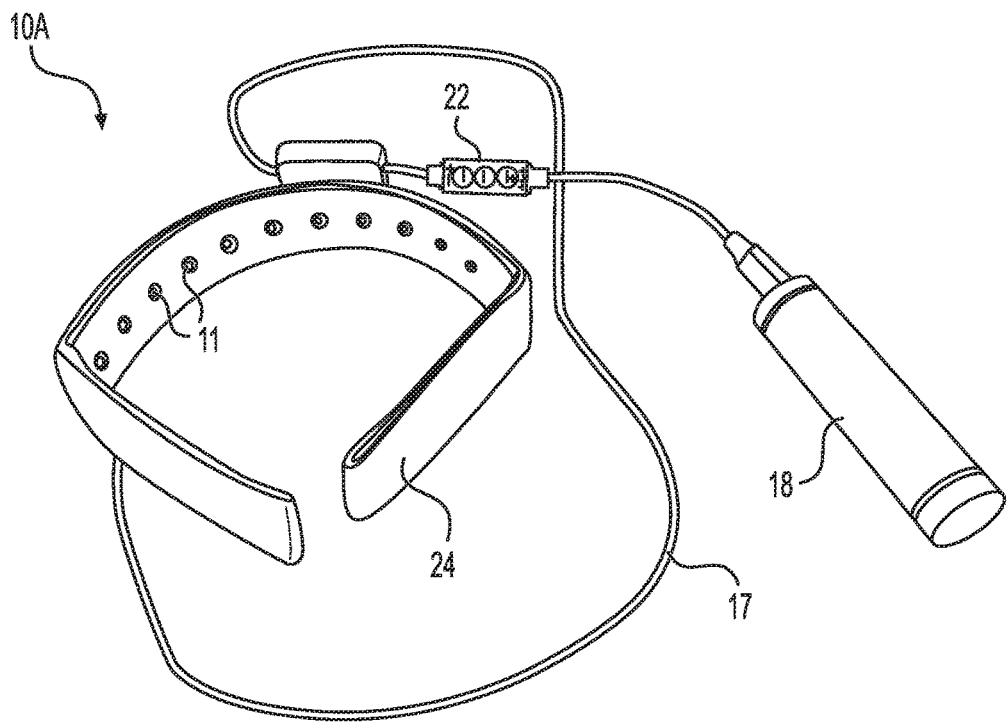
FIG. 4A is a schematic illustration of a system according to the invention with a device having straps for coupling to a subject's body.

FIG. 4A illustrates a system including a device 10A according the invention connected to a power source (battery) 18 via wire 17. A drive circuitry controller 22 regulates the power distributed to the LEDs 11. Velcro®-type straps 24 are connected to the device to facilitate attachment to a target region of a subject's body.

Figure 4B:
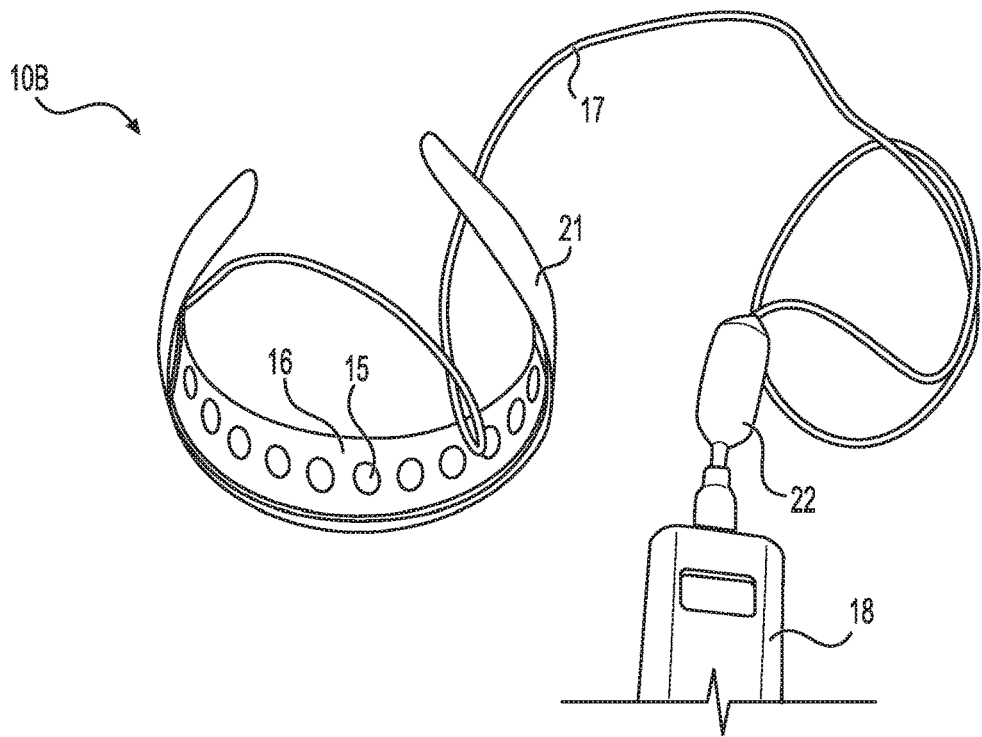
FIG. 4B is a schematic illustration of another system according to the invention with a device having a contoured shape-memory element for coupling to a subject's body.

FIG. 4B shows an alternative construction of sealed LED array device 10B formed into a contoured shape (e.g., an arch shape) for application of light to a curved part of the body like the neck, knee, ankle, elbow or wrist. In the illustrated embodiment of FIG. 4B, a contoured element 21 forms a posterior component to impart a curved shape to the device. The contoured element can be molded into a shape or formed of a shape-memory material. The contoured element 21 can be metal or plastic and preferably holds it shape after allowing it to be opened or pushed close. The device 10B of FIG. 4B is also adapted to connect to a power source 18, typically a battery, by a wire 17 and also includes an LED controller 22 to regulate the electrical energy delivered to the LEDs in use.

In certain applications heat extraction may be desirable. In a simple embodiment the device can be held in place by a stretchable sleeve that has thermally conductive properties. Examples of this include compression garments that incorporate one or more thermally conductive metal components. The patch would be placed under the compression garment. Light from the patch would be directed down into the tissue, while waste heat would be conducted away from the device by conduction utilizing the conductive metal (e.g., copper fibers incorporated into the compression garment or band). Alternatively, a highly thermally conductive belt (e.g., with one or more copper braid strips) can hold the device in place.

Figure 5A:
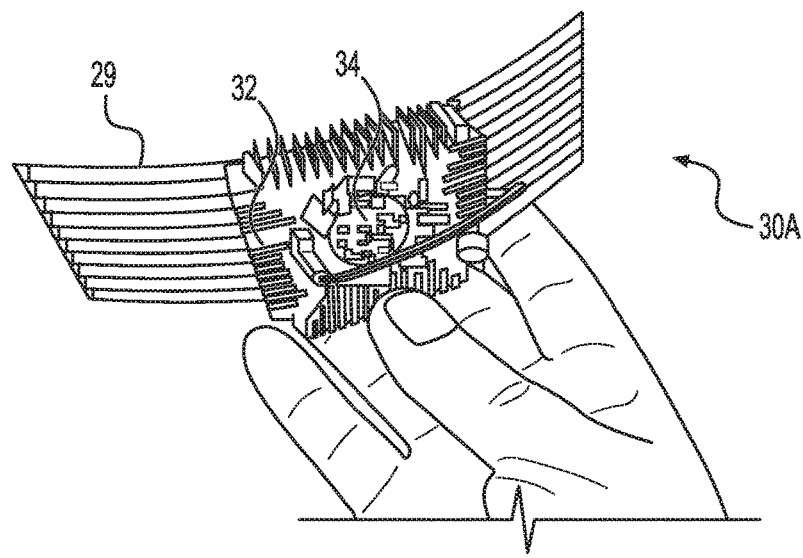
FIG. 5A is an illustration of a device according to the invention having fan-based cooling element.
Figure 5B:
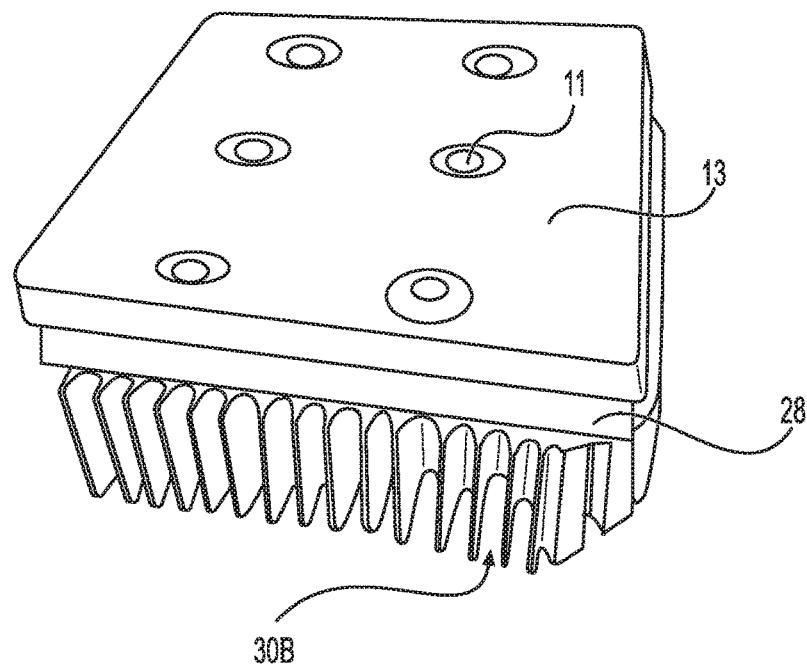
FIG. 5B is an illustration of a device according to the invention having Pelletier cooling element.

FIGS. 5A and 5B illustrate embodiments for higher power applications where active cooling of the device may be desired. In these embodiment, heatsinks are utilized to extract the surface heat from the tissue and/or the waste heat from the circuit board. An example of this is shown in FIG. 5A where the device includes a heat exchanger 30A including heat dissipating fins 32 and one or more fans 34. In addition (or in lieu of the fan) the device can further include conduits for circulation of a cooling fluid (not shown).

FIG. 5B illustrates yet another heat exchanger. In this embodiment, active cooling is accomplished by a thermoelectric (e.g., Pelletier) cooler 30B which can be secured to the posterior device surface (e.g., via a thermally-conductive adhesive 28). When current is run through the cooler 30B it lowers the temperature of the substrate 13 and can extract heat from the tissue. If the thermoelectric cooler is run simultaneously with the application of infrared radiation, the skin surface temperature can be controlled to prevent skin burning, while allowing deep heating of the muscle or fat cells. If the thermoelectric cooler is run alternately with the LED illumination one can get a cooling then heating cycle, desirable for certain muscular therapies.

In applications where it is desirable to control the temperature of the heated tissue, this can be accomplished by incorporating one or more thermistors into the device to make surface temperature measurements, or by incorporating an IR detector into the device to deduce the temperature of the heated tissue. Any of these techniques can be combined with the applied current to the circuit in a feedback loop to control the temperature to the desired point. Similarly, such control circuits can be used to safeguard the patient against the device or tissue overheating.

Figure 6A:
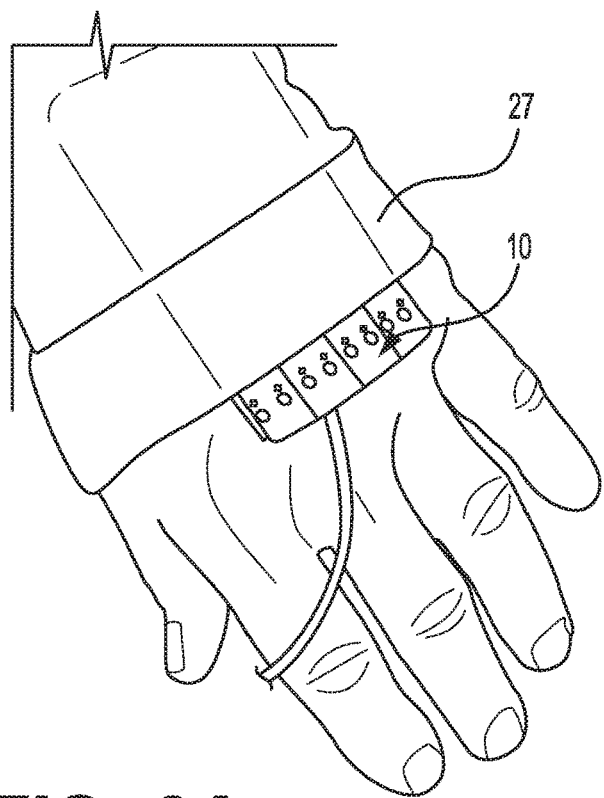
FIG. 6A is a schematic illustration of a device according to the invention coupled to a subject via a sleeve.
Figure 6B:
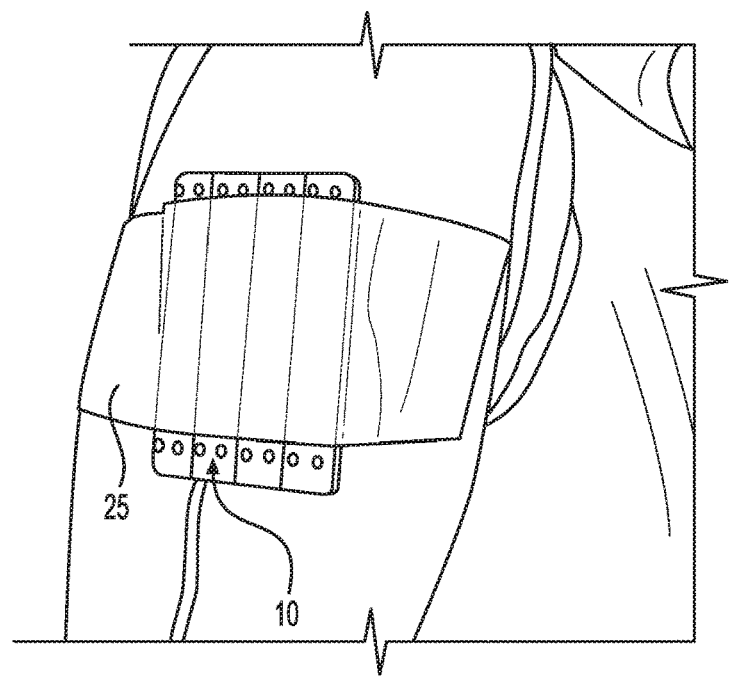
FIG. 6B is a schematic illustration of a device according to the invention coupled to a subject via adhesive tape.
Figure 6C:
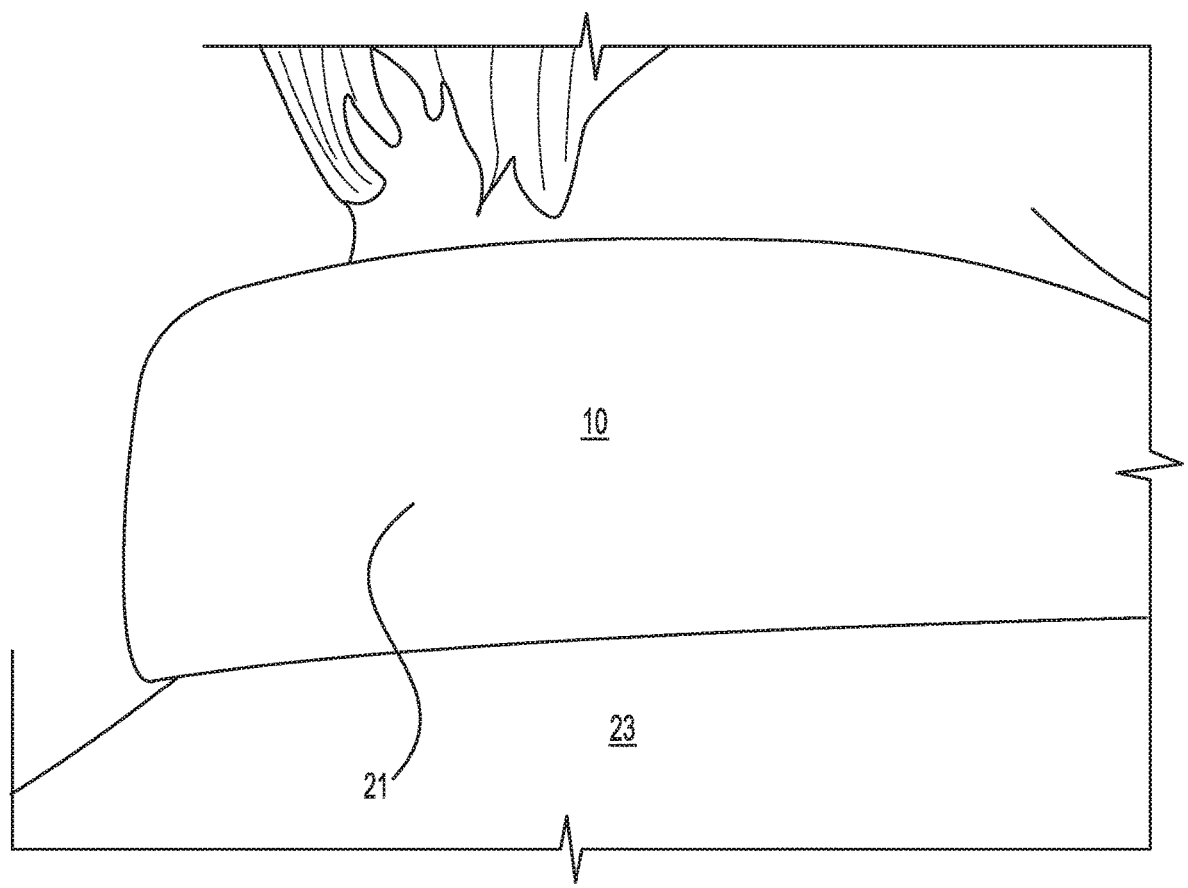
FIG. 6C is a schematic illustration of a device according to the invention coupled to a subject via a contoured shape-memory element.

FIG. 6A illustrates attachment of a device 10 according to the invention to a subject's hand or wrist by a sleeve 27. FIG. 6B illustrates attachment of a device 10 according to the invention to a subject's arm via adhesive tape 25. FIG. 6C illustrates attachment of a device 10 according to the invention to a subject's neck with a contoured or shape-memory element 23.

The invention claimed is:

1. A phototherapy device
comprising a flexible substrate,
a plurality of infrared light-emitting diodes (LED) light sources associated with the substrate and
drive circuitry connected to the light sources and configured to electrically couple the light sources to a power supply to distribute power to the light sources to emit infrared radiation,
wherein the substrate is adapted for positioning on a body of a patient to transmit infrared radiation to a target region of skin or muscle tissue of a subject to raise the temperature of the target region above normal body temperature, and
wherein the plurality of light sources are disposed in a spaced-apart relationship on the substrate such that they collectively emit infrared radiation in an overlapping pattern that provides for substantially uniform exposure of a target region, and
wherein the substrate comprises a reflective component positioned above or surrounding the light sources to return reflected or backscattered radiation back into the target region, and wherein a separation between any two neighboring ones of the light sources is about twice a distance at which a radiation power associated with at least one of the two neighboring light sources falls to about 37% of maximum radiation power emitted by that light source.

2. The device of claim 1 wherein the drive circuitry is disposed on the flexible substrate.

3. The device of claim 1 wherein the LED light sources emit infrared radiation of at least one wavelength in a range from 700 to 900 nanometers.

4. The device of claim 1 wherein the LED light sources emit radiation at about 805 nm.

5. The device of claim 1 wherein each light source generates about 25-1000 milliwatts of power when activated.

6. The device of claim 1 wherein each light source generates about 100-300 milliwatts of power when activated.

7. The device of claim 1 wherein the substrate comprises a plurality of recesses, into which the light sources are disposed.

8. The device of claim 1 wherein the substrate comprises silicone and the reflective component comprises reflective filler particles.

9. The phototherapy device of claim 8, wherein the reflective particles comprise any of titanium oxide and barium particles.

10. The device of claim 1 further comprising a light-transmissive sealing element at least partially covering an anterior surface of the substrate to isolate the LEDs from contact with a patient's skin.

11. The device of claim 1 further comprising a controller for adjustment of power levels to change the intensity of the emitted infrared radiation.

12. The phototherapy device of claim 11, further comprising at least one of a thermistor and a remote or embedded IR thermometry to monitor the temperature at the energy application site and adjust the power delivered to the light sources.

13. The device of claim 1 further comprising a power supply configured to couple to the drive circuitry.

14. The device of claim 1, wherein the device further comprises a sleeve coupling element configured to wrap around a body part, or an adhesive surface, or adhesive tape, or straps with hook and loop fasteners, or a contoured coupling element to hold the device in a desired position relative to the target region of a subject's body.

15. The device of claim 1 wherein the device further comprises a contoured coupling element that is curved to match the shape of the target region and, optionally, further comprises a shape-memory material.

16. The device of claim 1 wherein the device further comprises a sleeve or contoured coupling element having a thermally conductive element to dissipate heat during device operation.

17. The device of claim 1 wherein the device further comprises a heat extractor.

18. The device of claim 17 wherein the heat extractor is selected from the group of at least one fan, circulating fluid, heat dissipating fin, Peltier thermoelectric device or combinations thereof.

19. The phototherapy device of claim 1, wherein said reflective component comprises a white reflective sheet.

20. The phototherapy device of claim 1, wherein said reflective component comprises a diffusive sheet.

21. A method of providing phototherapy comprising
applying a flexible substrate carrying a plurality of infrared light sources to a body of a patient, the light sources being disposed in a spaced-apart relationship from each other on the substrate such that upon activation they collectively emit infrared radiation in an overlapping pattern that provides for substantially uniform exposure of a target region; and
activating the light sources to transmit infrared radiation to the target region of skin or muscle tissue of a subject to raise the temperature of the target region above normal body temperature,
wherein the substrate has a reflective component positioned above or surrounding the light sources and the method further comprises utilizing the reflective component to return reflected or backscattered radiation back into the target region,
wherein a separation between any two neighboring ones of the light sources is about twice a distance at which a radiation power associated with at least one of the two neighboring light sources falls to about 37% of maximum radiation power emitted by that light source.

22. The method of claim 21 further comprising delivering infrared radiation of at least one wavelength in a range from 700 nm to 900 nm.

23. The method of claim 21 wherein the step of activating the light sources further comprises generating about 50-1000 milliwatts of power per light source when activated.

24. The method of claim 21 wherein the step of activating the light sources further comprises generating about 100-300 milliwatts of power per light source when activated.

25. The method of claim 21 further comprising adjusting a power level of the light sources to change the intensity of the emitted infrared radiation.

26. The method of claim 21 further comprises deploying a sleeve adapted to wrap around a body part to hold the substrate and light sources in a desired position relative to the target region.

27. The method of claim 21 wherein the substrate or sleeve includes a thermally conductive element to dissipate heat.

28. The method of claim 21 wherein the method further comprises employing a controller for adjustment of power levels to change the intensity of the emitted infrared radiation.

29. The method of claim 28, further comprising at least one of a thermistor and a remote or embedded IR thermometry to monitor the temperature at an energy application site and adjust the power delivered to the light sources if necessary.

30. The method of claim 21 wherein the method further comprises cooling at least one of the substrate, light sources or patient body, either concurrently with the step of activating the light sources to transmit infrared radiation to the target region, or the step of cooling is performed before or following the step of activating the light sources to transmit infrared radiation to the target region.

31. A wearable device comprising
a substrate,
a plurality of infrared light-emitting diodes (LED) light sources associated with the substrate, and
drive circuitry connected to the light sources and configured to electrically couple the light sources to a power supply to distribute power to the light sources such that the light sources emit infrared radiation for illuminating a target tissue portion of a wearer of the device, wherein the plurality of light sources is disposed in a spaced-apart relationship on the substrate such that a separation between any two neighboring ones of the light sources is about twice a distance at which a radiation power associated with at least one of the two neighboring light sources falls to about 37% of maximum radiation power emitted by that light source.

32. The wearable device of claim 31, further comprising a reflective component positioned above or surrounding the light sources to return reflected or backscattered radiation back to the target tissue.

33. The wearable device of claim 31, wherein the substrate is flexible and is adapted for positioning on a body portion of the wearer of the device.

34. A wearable device comprising
a substrate,
a plurality of infrared light-emitting diodes (LED) light sources associated with the substrate,
drive circuitry connected to the light sources and configured to electrically couple the light sources to a power supply to distribute power to the light sources such that the light sources emit infrared radiation for illuminating a target tissue portion of a wearer of the device, and
a white reflective sheet positioned above or surrounding the light sources to return reflected or backscattered radiation back into the target region,
wherein the plurality of light sources is disposed in a spaced-apart relationship on the substrate such that a separation between any two neighboring ones of the light sources is about twice a distance at which a radiation power associated with at least one of the two neighboring light sources falls to about 37% of maximum radiation power emitted by that light source.

35. The wearable device of claim 34, wherein the reflective sheet comprises a diffusive sheet.

* * * * *